US011266534B2

(12) United States Patent
Gogolowski et al.

(10) Patent No.: US 11,266,534 B2
(45) Date of Patent: Mar. 8, 2022

(54) EXTENSIBLE DRESSINGS

(71) Applicant: Johnson & Johnson Consumer Inc., Skillman, NJ (US)

(72) Inventors: Marisha Gogolowski, Philadelphia, PA (US); Carmine Rizzo, Port St. Lucie, FL (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 512 days.

(21) Appl. No.: 15/950,359

(22) Filed: Apr. 11, 2018

(65) Prior Publication Data
US 2018/0289557 A1  Oct. 11, 2018

Related U.S. Application Data

(60) Provisional application No. 62/483,992, filed on Apr. 11, 2017.

(51) Int. Cl.
*A61F 13/00* (2006.01)
*A61F 13/02* (2006.01)
*A61F 13/06* (2006.01)
*A61F 13/10* (2006.01)

(52) U.S. Cl.
CPC ........ *A61F 13/00038* (2013.01); *A61F 13/00* (2013.01); *A61F 13/00021* (2013.01); *A61F 13/0233* (2013.01); *A61F 13/0243* (2013.01); *A61F 13/0263* (2013.01); *A61F 13/0266* (2013.01); *A61F 13/061* (2013.01); *A61F 13/10* (2013.01); *A61F 2013/00595* (2013.01); *A61F 2013/00604* (2013.01); *A61F 2013/00655* (2013.01)

(58) Field of Classification Search
CPC .......... A61F 13/00038; A61F 13/00021; A61F 13/0233; A61F 13/0243; A61F 13/0263; A61F 13/0266; A61F 13/061; A61F 13/10; A61F 2013/00595; A61F 2013/00604; A61F 2013/00655; A61F 13/00068; A61F 13/00046; A61F 2013/00217; A61F 13/148; A61F 13/14; A61F 13/15; A61F 5/03
See application file for complete search history.

(56) References Cited

U.S. PATENT DOCUMENTS

| 4,541,426 | A |   | 9/1985  | Webster      |            |
|-----------|---|---|---------|--------------|------------|
| 4,612,230 | A |   | 9/1986  | Liland et al.|            |
| 5,264,218 | A | * | 11/1993 | Rogozinski   | A61F 13/023 |
|           |   |   |         |              | 424/443    |
| 5,267,952 | A |   | 12/1993 | Gardner      |            |
| 5,397,316 | A | * | 3/1995  | LaVon        | A61F 13/535 |
|           |   |   |         |              | 604/369    |

(Continued)

FOREIGN PATENT DOCUMENTS

CN        1807084 A      7/2006
CN     201492576 U      6/2010
(Continued)

OTHER PUBLICATIONS

International Search Report, dated Jun. 18, 2018, PCT/US2018/027026.

Primary Examiner — Camtu T Nguyen

(57) ABSTRACT

The present invention generally relates to dressings such as bandages or tapes having improved extensibility and conformability to human skin and joints.

19 Claims, 10 Drawing Sheets

(56) References Cited

U.S. PATENT DOCUMENTS

| | | | |
|---|---|---|---|
| 5,714,225 A | | 2/1998 | Hansen et al. |
| 5,919,411 A | | 7/1999 | Rezai et al. |
| 5,981,822 A | * | 11/1999 | Addison ............. A61F 13/0203 602/41 |
| 7,790,946 B2 | * | 9/2010 | Mulligan ............ A61F 13/0203 602/57 |
| 8,236,083 B2 | | 8/2012 | Garcia et al. |
| 8,680,360 B2 | | 3/2014 | Greener et al. |
| 2009/0099519 A1 | * | 4/2009 | Kaplan ............... A61M 1/0088 604/113 |
| 2012/0041402 A1 | * | 2/2012 | Greener ............ A61F 13/00987 604/319 |
| 2013/0245527 A1 | | 9/2013 | Croizat et al. |
| 2017/0258640 A1 | * | 9/2017 | Ahsani Ghahreman ..................... A61F 13/02 |

FOREIGN PATENT DOCUMENTS

| | | |
|---|---|---|
| CN | 203953946 U | 11/2014 |
| EP | 0 300 815 A2 | 1/1989 |
| JP | 2007167096 A | 7/2007 |
| JP | 6043566 B | 12/2016 |
| KR | 20150057669 A | 5/2015 |

\* cited by examiner

EXTENSIBLE DRESSINGS

CROSS-REFERENCE TO RELATED APPLICATION

The present application claims the benefit of the earlier filing date of U.S. provisional patent application 62/483,992, filed Apr. 11, 2017, the entirety of which application is hereby incorporated by reference herein as if fully set forth herein.

FIELD OF THE INVENTION

The present invention generally relates to dressings such as bandages or tapes having improved extensibility and conformability to human skin and joints. In certain embodiments, the present invention relates to dressings that include, at least one layer of material, a portion of which layer of material includes a plurality of material free regions extending through the thickness of the portion. In at least one exemplary embodiment, the plurality of the material free regions is arranged in the form of a pattern of concentric slitted annuli having a common center point, P, the pattern of concentric slitted annuli having, relative to the center point P, a radially innermost concentric annulus and a radially outermost concentric annulus respectively having the shortest and the longest diameters.

BACKGROUND OF THE INVENTION

Dressings such as bandages and tapes for applying to and/or covering the skin have been known for some time. Such dressings have gained wide acceptance for closing minor wounds, protecting minor wounds and/or covering abrasions. In some instances, microporous or breathable, bandages or tapes have been developed and are used either to cover minor wounds or wounds that have been partially healed.

While such dressings have been greatly improved over the years in that, for example, they have incorporated microporous materials allowing the wound to breath and permitting water vapor to escape from the wound, hence, reducing chances of wound maceration, there remains a need for a dressing which provide improved extensibility and elasticity of the dressing such that the dressing will cover and accommodate the dimensional contours of skin or tissues and move with (i.e., accommodating movement of) that portion of the skin or tissues covered by or in contact with the dressing, particularly in the situation where the dressing covers or is in contact with areas of the human tissue associated with jointed regions such as the joints of the fingers, ankles or knees. Accordingly, in order for a dressing to provide the aforementioned attributes, the dressing should also be able to dynamically conform to and with changing three dimensional contour of the skin or tissue surfaces to which it is applied.

The dressing should also be conformable to, or provide sufficient drapability, over the area of the human skin tissue to which it is adhered.

It is, therefore, an aspect of the present invention to provide dressings that may be used to cover, protect wounds and facilitate wound healing. It is a further aspect of the present invention to provide bandages and tapes that conform to a wounded area of the skin and have improved extensibility, elasticity and conformability for better coverage of movable areas such as joints. Other aspects of the present invention will be readily apparent from the ensuing description and claims.

SUMMARY OF THE INVENTION

In one embodiment, the present invention relates to a dressing comprising:
a layer of non-cellulosic material having:
 (i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
 (ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters,
wherein the plurality of the material free regions is arranged end to end, separated by a plurality of spatial intervals, such that any material free region In located in any concentric annulus I subtends a non-zero valued angle, $\alpha_{I_n}$, at the center point P, where n represents the number identifying a material free region in an annulus having material free regions arranged numerically consecutively in such annulus,
wherein the sum of the non-zero valued angles subtended by the plurality of the material free regions at the center point P, within any one of the concentric annuli, is less than 360 degrees, and
wherein the material free regions of any one of the concentric annuli are in a radially staggered relation with respect to the material free regions in any adjacent inner and/or adjacent outer concentric annulus.

The present invention also relates to methods of using/applying the dressings of the present invention, including the disclosed embodiments, on skin surfaces covering jointed areas (or areas prone to movement) of human or mammalian bodies.

BRIEF DESCRIPTION OF THE DRAWINGS

An embodiment of this invention will now be described in greater detail, by way of illustration only, with reference to the accompanying drawings, in which:

FIG. 4A shows a planar view of the pattern of concentric slitted annuli of FIG. 2A with centerlines of each annulus of the concentric slitted annuli drawn-in;

DETAILED DESCRIPTION OF THE INVENTION

Figure 1:
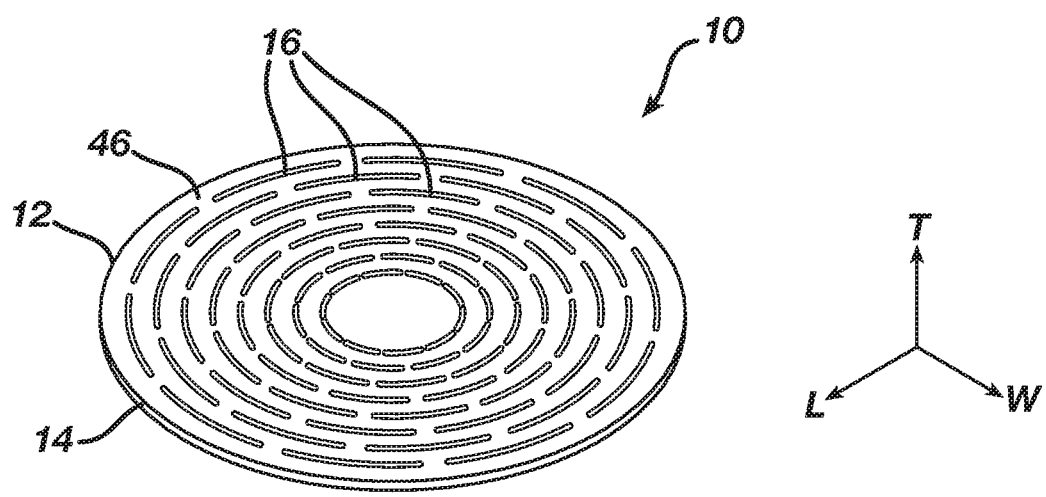
FIG. 1 shows a perspective view of a layer of material including a plurality of material free regions arranged in the form of a pattern of concentric slitted annuli.

The dressing of the present invention can comprise, consist of, or consist essentially of the essential elements and limitations of the invention described herein, as well as any of the additional or optional features, components, or limitations described herein.

The term "comprising" (and its grammatical variations) as used herein is used in the inclusive sense of (and, interchangeably with the terms) "having" or "including" and not in the exclusive sense of "consisting only of." The terms "a" and "the" as used herein are understood to encompass the plural as well as the singular.

As used here in the specification and the claims, the terms "skin" and "tissue" are interchangeable and refer to mammalian skin.

As used here in the specification and the claims, the term "dermatologically acceptable" means suitable for use in contact with skin tissue without undue toxicity, incompatibility, instability or adverse reaction with the skin tissue.

As used here in the specification and the claims, the terms "proximate", "neighboring", "adjacent", and any variants thereof, are used interchangeably in connection with the present invention.

As used here in the specification and the claims, the term "annulus" denotes a circular profile/shape, e.g., a circle, or a non-circular profile/shape, such as an ellipse, or any polygonal shape that approximates a circle or an ellipse shape.

As used here in the specification and the claims, the term "concentric centerline", of any given concentric annulus, denotes an imaginary line that is either coincident with a circumference (e.g., passes through midpoints of an annular path) of the concentric annulus or an imaginary line that intersects at least a segment of each of a plurality of material free regions that are arranged end to end at a spatial, in some embodiments predetermined, interval to form the concentric annulus.

As used herein, the terms "visual inspection" or "visually inspected" means inspection with the unaided eye (excepting standard corrective lenses adapted to compensate for near-sightedness, farsightedness, or stigmatism, or other corrected vision) in lighting at least equal to the illumination of a standard 75 watt incandescent white light bulb at a distance of about 0.25 meter.

All documents incorporated herein by reference, by portion or in their entirety, are only incorporated herein to the extent that they are not inconsistent with this specification.

In certain embodiments, the present invention as disclosed herein may be practiced in the absence of any component, element (or group of components or elements) or method step which is not specifically disclosed herein.

An embodiment of this invention will now be described in greater detail, by way of illustration only, with reference to the accompanying drawings. Referring to the drawings in detail, wherein like reference numerals indicate like elements throughout, there is shown in FIGS. 1-5, a dressing, generally designated with reference numeral 10, in accordance with an exemplary embodiment of the present invention.

Layer of Material

Referring to FIG. 1, in an exemplary embodiment, the dressing 10 includes a layer of material 12 having a length direction (L), a width direction (W), and a thickness direction (T) respectively defining axes in three mutually orthogonal directions, the length direction (L) and the width direction W jointly defining a horizontal plane ("the LW plane"), and the thickness direction T defining an up-down direction or a vertical direction relative to the LW plane and top and bottom (skin facing) surfaces. In one embodiment, as illustrated in FIG. 1, the layer of material 12 has a thickness 14 taken in the thickness direction T. In addition to the circular shape indicated in the figures, the layer of material can take the form of any number of shapes, including but not limited to, rectangular, oval, ovoid, or oblong etc.

In certain embodiments, the layer of material is formed from cellulosic material, the cellulosic material comprising fibers having a length to diameter ratio of greater than, or equal to, 600.

In other embodiments, the layer of material is formed from non-cellulosic or regenerated cellulose material. The term "non-cellulosic" with respect to the material means that the material contains less than 10 wt %, optionally containing less than 5 wt %, optionally containing less than 1 wt %, optionally containing less than 0.1 wt %, or optionally containing 0 wt %, of cellulosic components or fibers. The term "regenerated cellulose" with respect to the material means the material contains less than 10 wt %, optionally containing less than 5 wt %, optionally containing less than 1 wt %, optionally containing less than 0.1 wt %, or optionally containing 0 wt %, of non-regenerated cellulose components or fibers. Suitable materials include, but are not limited to, (or selected from or selected from the group consisting of) polyurethanes, polyethylene, polyisobutadiene, polyisobutylene, neoprene, polyamides, polyesters (such as polyethylene terephthalate (PET), polybutylene terephthalate (PBT) and mixtures thereof), polyether polyesters, non-hydrophilic polyether-polyamides, plasticised polyvinyl chloride, styrene-butadiene block copolymers, styrene-isoprene block copolymer, polyacrylates, methacrylic copolymers, polypropylene, rayon, rayon/polyester blends and mixtures thereof. In certain embodiments, the material is a dermatologically acceptable material.

Material Free Regions

Figure 2:
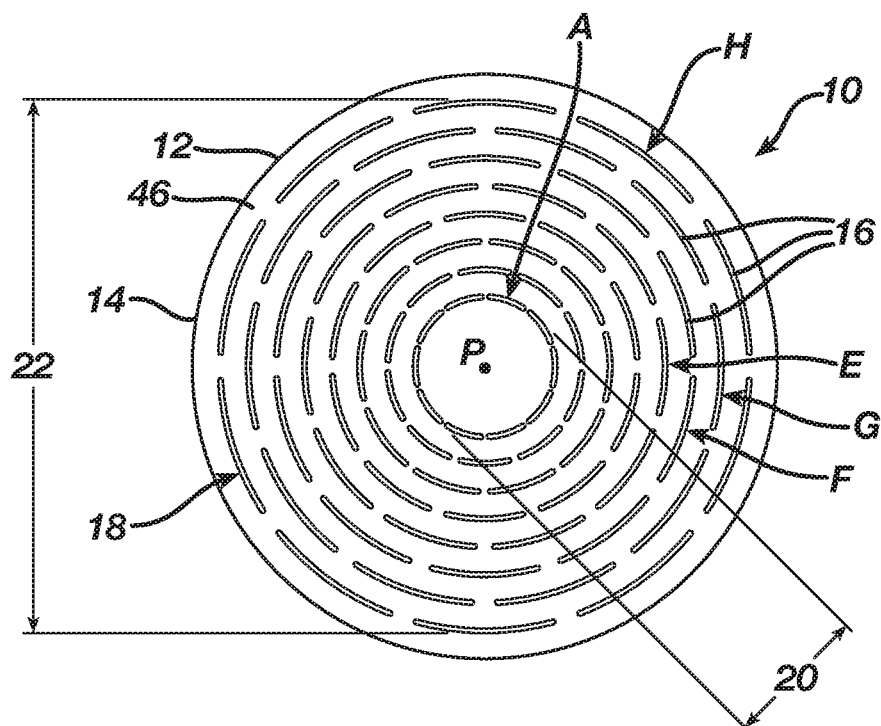
FIG. 2 shows a planar view of a layer of material including a plurality of material free regions arranged in the form of a pattern of concentric slitted annuli.
Figure 2A:
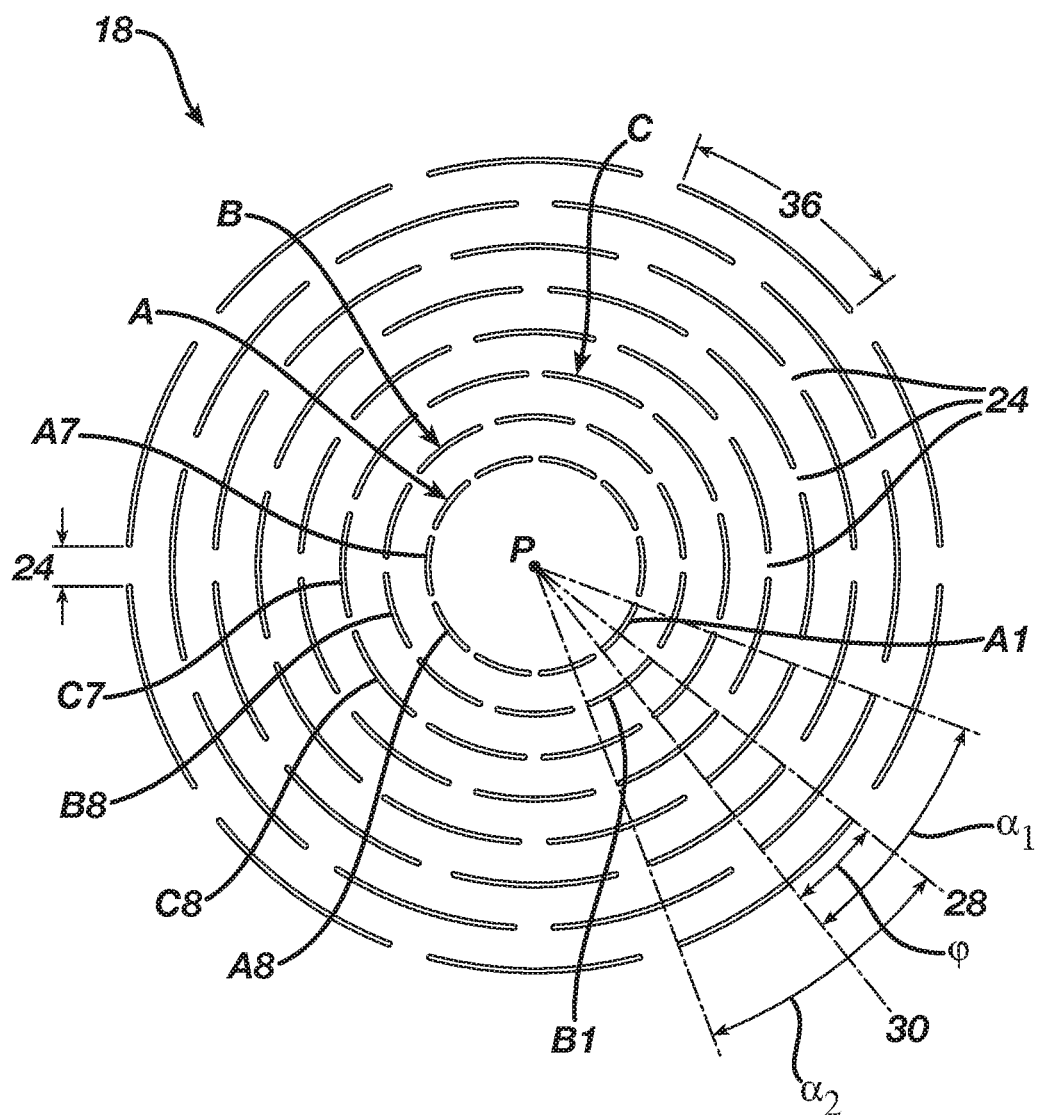
FIG. 2A shows a planar view of a pattern of concentric slitted annuli.

In one embodiment, as illustrated in FIGS. 1 and 2A, the layer of material 12 of the dressing 10 includes a plurality of material free regions 16 each of which extends through the thickness 14 of at least a portion of the layer of material 12. The term "material free" or "free of material" as used herein means regions or areas of the layer of material that are free of material or substantially free of material such that the continuity of the material is disrupted or such regions or areas are devoid of material and include, and interchangeable with, but not limited to, cuts, holes, slits (or slitted) or openings in the material. In certain embodiments, the distinct material free regions 16 are sigmoidal in shape and include such distinct regions which may not be discernable by the naked eye (i.e., viewing without the aid of optical lenses which magnify the field of view); examples of such include ultra-thin cuts or slits formed in the layer of material 12 by cutting the layer of material 12 with a knife thickness of about 1 μm to about 15 μm, or a laser having laser thickness of about 10 μm to 1000 μm. The material free regions can be in the form of any number of shapes. In certain embodiments, as illustrated in FIGS. 1-3 and FIG. 6, these material free regions 16 in the layer of material 12 can be in the form of individual arcs or sigmoidal slits, respectively.

In addition to lasers and knifes, the material free regions may also be incorporated into the layer of material 12 during the formation of the layer of material 12 such as by water jet cutting, high pressure steam cutting and the like.

Figure 2B:
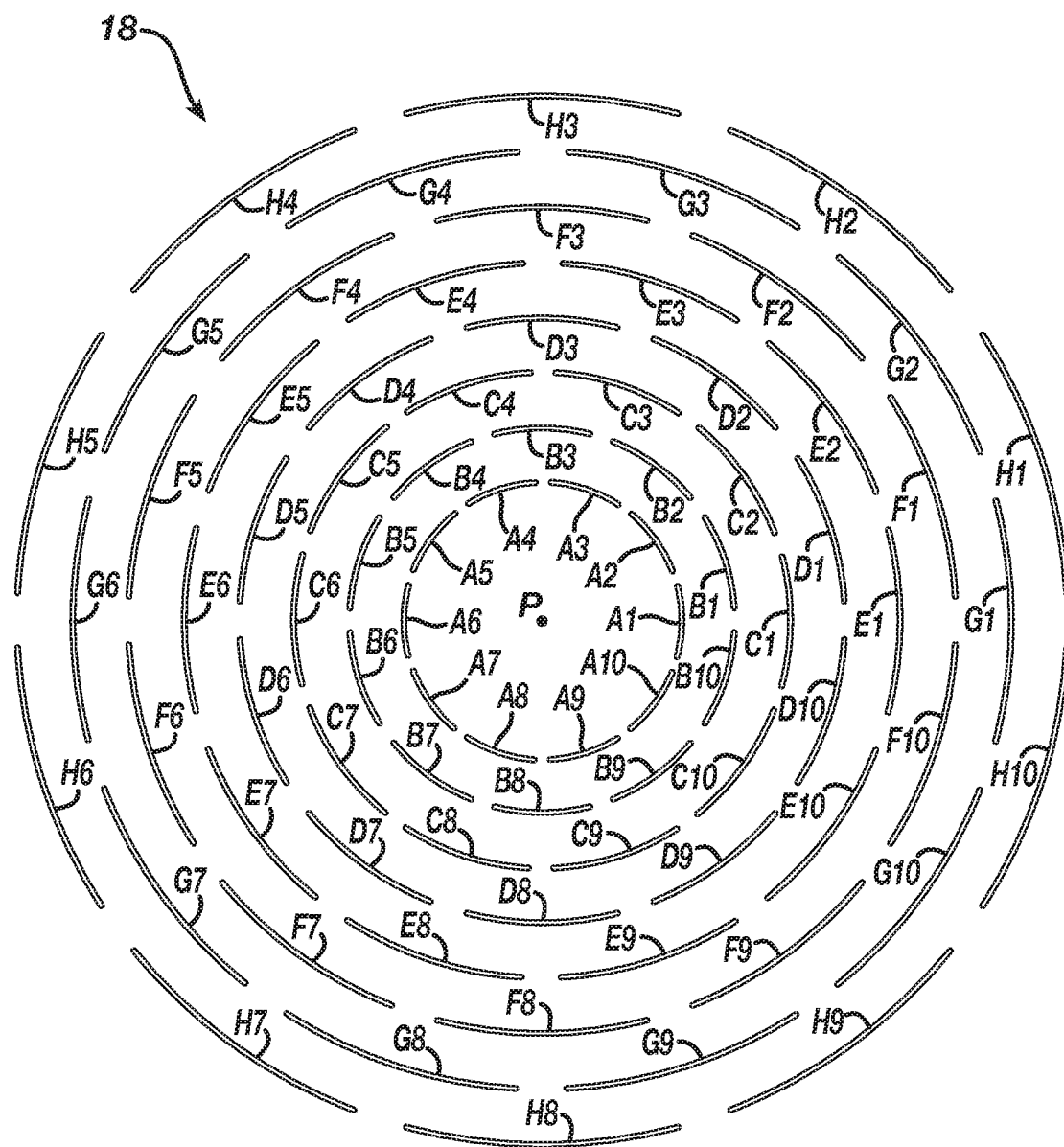
FIG. 2B shows another planar view of a pattern of concentric slitted annuli of FIG. 2A with each material free region labeled.

In one embodiment, as illustrated in FIGS. 2B and 2C, the plurality of the material free regions 16 is arranged as slits in the form of a pattern of slitted concentric annuli 18 having a center point (P) in the LW plane of the layer. In one embodiment, as in FIG. 2A, the pattern of concentric slitted annuli 18 is depicted as having eight annuli labeled A to H from innermost concentric annulus A to the outermost concentric annulus H. However, it should be understood that the number of annuli in the pattern of concentric slitted annuli 18 can be any number above 1, including 2, 3, 4, 5, and so on. Depending on the particular application and/or specific nature of the material used for the dressing 10 the pattern of concentric slitted annuli 18 may include any number of concentric annuli, all within the purview of one skilled in the art.

Referring to FIGS. 1-2B, in one exemplary embodiment, the layer of material 12 includes a pattern of concentric slitted annuli 18 in which each concentric annulus includes a number n of the plurality of the material free regions 16. The number n of material free regions in any given concentric annulus can be any suitable number so long as it would result in a dressing having at least one or more of the properties described in this application and so long as the innermost concentric annulus A comprises at least two material free regions 16. In one embodiment, as illustrated in FIG. 2B, the same number of the material free regions 16 exists in each of the concentric annuli A-H. However, it should be understood that the number n of material free regions 16 may vary among the concentric annuli of the pattern of concentric slitted annuli 18. In some embodiments, the number n of the material free regions 16 ranges from 2 to 25, optionally from 2 to 18, optionally from 2 to 7, optionally from 3 to 7.

In some embodiments, the number n of the material free regions 16 in any given concentric annulus ranges from 3 to 10.

Referring to FIG. 2A, in one embodiment, the plurality of the material free regions 16 is arranged end to end separated by spatial intervals 24. In particular, the plurality of the material free regions 16 is arranged sequentially along an annular path such that the material free regions 16 are separated by spatial intervals 24 from each other and each of the material free regions 16 subtends an angle, α, (e.g., $\alpha_1$ and $\alpha_2$) at the center point P of the pattern of concentric slitted annuli 18. The angle α that is subtended at the center point P by any given material free regions 16 can have a value ranging from about 20° to about 177°, optionally from 20° to 90°, optionally from 30° to 60°. Typically, the sum of the angles subtended at the center point P by the plurality of the material free regions 16 within any given concentric annulus is less than 360 degrees but more than 0 degrees. This ensures presence of the spatial intervals 24 between the material free regions 16.

In at least one embodiment, as further illustrated in FIG. 2B, the material free regions 16 of any one of the concentric annuli 18 are disposed in radially staggered relation (i.e., not aligned) with respect to the material free regions 16 of any adjacent inner and/or adjacent outer concentric annulus. The material free region A1 of the innermost concentric annulus A, for example, is in a staggered relation with proximate material free regions B1 and B10 of adjacent intervening concentric annulus B. Similarly, the material free region C1 of intervening concentric annulus C, for example, is in a staggered relation with proximate material free regions D1 and D10 of adjacent intervening concentric annulus D and also with proximate material free regions B1 and B10 of adjacent intervening concentric annulus B. Similarly, the material free region H1 of outermost concentric annulus H, for example, is in a staggered relation with proximate material free regions G1 and G2 of adjacent intervening concentric annulus G. Thus, each of the material free regions of any concentric annulus that is adjacent to a radially inner concentric annulus and a radially outer concentric annulus is adjacent, and staggered with respect, to four material free regions, two in the adjacent radially inner concentric annulus and two in the adjacent radially outer concentric annulus. In contrast, each of the material free regions in the innermost concentric annulus or the outermost concentric annulus is only adjacent, and staggered with respect, to two material free regions in a neighboring concentric annulus since each of the innermost and outermost concentric annuli is adjacent to only one concentric annulus.

The staggered arrangement described above is further illustrated in FIG. 2A, where any material free region 16 of any one of the concentric annuli of the pattern of concentric slitted annuli 18 has an axis of symmetry which bisects such material free region 16 and the corresponding material free region 16 of the radially innermost concentric annulus to which it is aligned. Such axis of symmetry also bisects the angle subtended by such material free region 16 and the corresponding material free region 16 of the radially innermost annulus to which it is aligned at the center point P. For example, the material free region 1C of concentric annulus C has an axis of symmetry 28 which bisects material free region 1C and also bisects material free region 1A of innermost concentric annulus A with which it is aligned; the axis of symmetry 28 also bisects angle $\alpha_1$ subtended by the material free regions 1C and 1A at the center point P. Similarly, material free region 1D of concentric annulus D has an axis of symmetry 30 which bisects material free region 1D and also bisects material free region 1B of innermost concentric annulus B with which it is aligned; the axis of symmetry 30 also bisects angle $\alpha_2$ subtended by the material free regions 1D and 1B at the center point P. The axis of symmetry 28 of one set of aligned material free regions 16 is staggered relative to axis of symmetry 30 of the other set of aligned material free regions 16 by an angle $\varphi$. Generally, the axis of symmetry 28 of aligned material free regions 1A and 1C of concentric annuli A and C and the axis of symmetry 30 of aligned material free regions 1B and 1D of concentric annuli B and D are staggered relative to one another by an angle $\varphi$ which has a value that generally falls within a range specified by the equation: $0°<\varphi<(\alpha_1+\alpha_2)$, wherein $\alpha_1$ is the angle subtended by the material free regions 1A and 1C at the center point P and $\alpha_2$ is the angle subtended by the material free regions 1B and 1D at the center point P. The angle $\varphi$ can have any suitable non-zero value, including values ranging from about 5° to 40°, optionally from about 5° to 30°, optionally from about 5° to 25°, optionally from about 5° to 20°, optionally from about 10° to 20°. For any intervening concentric annulus between the innermost concentric annulus A and outermost concentric annulus H, any material free region 16 is proximate to two material free regions 16 located in an adjacent concentric, radially inner annulus and two material free regions 16 located in an adjacent concentric, radially outer annulus with respect to the intervening concentric annulus. Accordingly, as shown in the embodiment of FIG. 2B, material free region B8 of intervening concentric annulus B is proximate to material free regions A8 and A9 of the innermost concentric annulus A and material free regions C8 and C9 of the intervening concentric annulus C. Moreover, material free region B8 of intervening concentric annulus B has an axis of symmetry (bisecting the angle subtended by the material free region B8 at the center point P) that is staggered by angle $\varphi$ relative to each of the respective axes of symmetry of proximate material free regions A8, A9, C8 and C9.

Accordingly:
(a) any material free region In located in any concentric annulus I subtends a non-zero valued angle $\alpha_{In}$ at the center point P and has an axis of symmetry that bisects the non-zero valued angle $\alpha_{In}$;
(b) any material free region Kn located in any concentric annulus K that is adjacent to concentric annulus I and proximate to material free region In, subtends a non-zero valued angle $\alpha_{Kn}$ at the center point P and has an axis of symmetry that bisects the non-zero valued angle $\alpha_{Kn}$;
(c) the axis of symmetry of the material free region In is staggered by an angle $\varphi$ from the axis of symmetry of the material free region Kn; and
(d) the angle $\varphi$ has a value that falls within a range specified by the equation: $0°<\varphi<(\alpha_{In}+\alpha_{Kn})$ where n represents the number identifying a material free region in an annuli having material free regions arranged numerically consecutively in such annuli (as shown in FIG. 2B, for example, in the case of F1 through F10 for annulus F).

By way of illustration, for n=8, the material free region F8 of annulus F would subtend an angle $\alpha_{F8}$ at the center point P and a material free region adjacent and proximate to F8, such as E8 (or E9), of adjacent annulus E would likewise subtend angle $\alpha_{E8}$ (or $\alpha_{E9}$ in the case of E9) at the center point P and the axis of symmetry of F8 and E8 (or E9) would, respectively, bisect angles $\alpha_{F8}$ and $\alpha_{E8}$ (or $\alpha_{E9}$ in the case of E9). It should be understood that material free regions G8 and G9 of annulus G (adjacent to F) would also be considered adjacent and proximate to F8 and, similarly, subtending and bisecting their respective angles $\alpha_{G8}$ and $\alpha_{G9}$ at the center point P.

As noted elsewhere in this application, the angle $\varphi$ can have any suitable non-zero value, including values ranging from 5 optionally from about 5° to 40°, optionally from about 10° to 40°, optionally from 10° to 30°.

As evident in FIG. 2, the concentric annuli of the pattern of concentric slitted annuli 18 have radii that increase in value relative to the center point P of the pattern of concentric slitted annuli 18 moving from the radially innermost concentric annulus A (having the shortest radius) to the radially outermost concentric annulus H (having the longest radius). In other words, in any pattern of concentric slitted annuli 18 the innermost concentric annulus A will have the shortest diameter (e.g., diameter 20) and the outermost concentric annulus H will have the longest diameter (e.g., diameter 22).

Figure 4A:
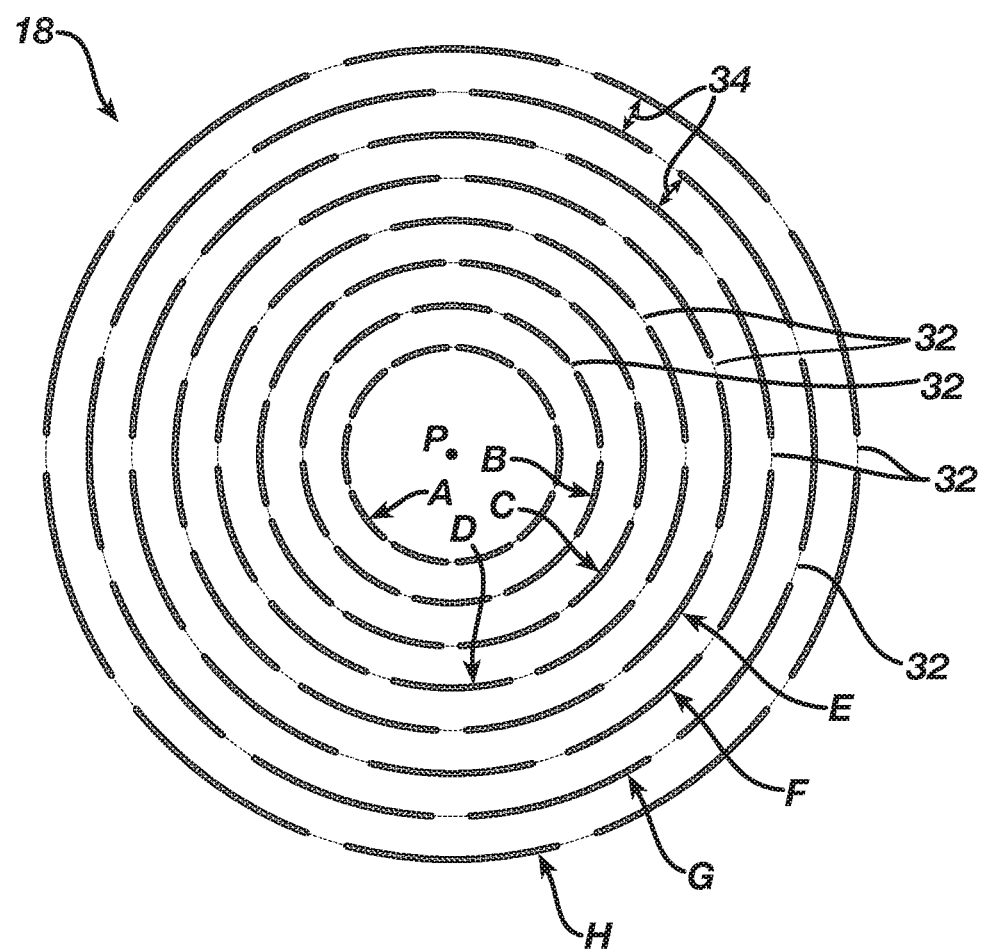

Referring to FIG. 4A, each concentric annulus of the concentric annuli of the pattern of concentric slitted annuli 18 is radially spaced apart from any adjacent inner or outer concentric annulus with respect to the concentric annulus (see reference numeral 34). Also, each concentric annulus has a concentric centerline defined therethrough as indicated, for example, by the dashed concentric centerline referenced by numeral 32 in FIG. 4A. The term concentric centerline, of any given concentric annulus, denotes an imaginary line that is either coincident with a circumference (e.g., passes through midpoints of an annular path as in FIG. 4A) of the concentric annulus of the pattern of concentric slitted annuli 18 or an imaginary line that intersects at least a segment of each of the plurality of the material free regions 16 that are arranged end to end separated by a spatial interval to form the concentric annulus (as shown by the dashed concentric centerline referenced by numeral 32 for the innermost concentric annulus in FIG. 5). Any pair of neighboring concentric centerlines of adjacent concentric annuli is radially spaced apart from each other by a distance that is the difference between the lengths of the respective radii of the adjacent concentric annuli or the difference between the distances of the respective centerlines of the adjacent concentric annuli as measured from the center point P (e.g., FIG. 4A, reference numeral 34).

Figure 4B:
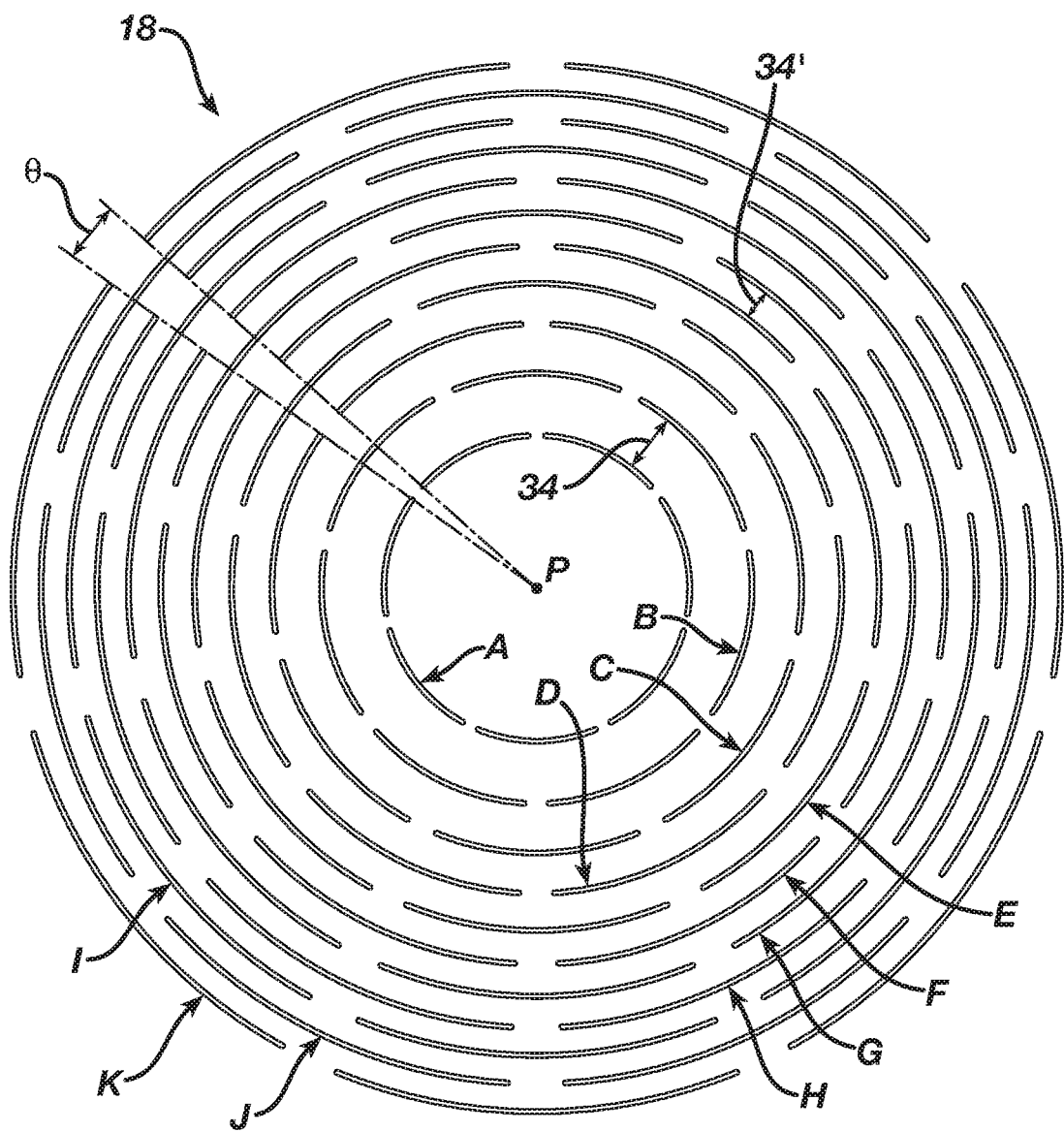
FIG. 4B shows a planar view of a pattern of concentric slitted annuli.

In one embodiment, as illustrated in FIG. 4A, the radial distances 34 between neighboring pairs of concentric centerlines of successive pairs of neighboring annuli of the pattern of concentric slitted annuli 18 can be substantially equal to each other or different from each other. In other embodiments, any pair of neighboring annuli is separated by a radial spacing 34 (measured as a distance between concentric centerlines of the pair of neighboring annuli) that varies among any different pairs of centerlines of other successive pairs of neighboring annuli of the pattern of concentric slitted annuli 18. In one embodiment, the radial spacing 34 between pairs of neighboring centerlines of neighboring annuli has a value that is at its minimum between the innermost concentric annulus and its neighboring concentric annulus and increases radially outwardly to its maximum value between the outermost concentric annulus and its neighboring concentric annulus. In one embodiment, as illustrated in FIG. 4B, the radial spacing 34 between pairs of neighboring centerlines of neighboring annuli has a value that is at its maximum between the innermost concentric annulus and its neighboring concentric annulus and, as also illustrated in FIG. 4B, the radial spacing 34 decreases radially outwardly to its minimum between the outermost concentric annulus and its neighboring concentric annulus (compare reference numerals 34 and 34'). However, other configurations for the radial distances between adjacent concentric annuli are possible. Accordingly, in some embodiments, the pattern of concentric slitted annuli 18 has a radial spacing 34 between concentric centerlines of successive pairs of neighboring annuli that varies among different pairs of neighboring concentric annuli such that the magnitudes of successive radial spacings are not necessarily arranged in an ascending or a descending order but in some random order.

Typically, the radial distance 34 between a pair of concentric annuli of the pattern of concentric slitted annuli 18 has a value that ranges from 0.01 inches to 1.0 inches, optionally from 0.01 inches to 0.5 inches from 0.01 inches to 0.25 inches; 0.01 inches to 0.125 inches.

An ideal dressing should provide an optimal healing environment that can promote new cell growth and/or healing when appropriate. Additionally, or in other situations, the dressing may be required to protect the site of application from trauma, to administer medicine, to absorb exudate, to keep wounds, pressure sores, ulcers, warts or lesions clean, and/or to stop bleeding. Also, depending on its location on the body surface, the environment of the wound, pressure sore, ulcer, wart or lesion, may be subjected to frequent stress, strain, or a combination of stress and strain as the three dimensional contour of the covered skin surface site or the skin surface around the covered site changes in response to movements of tissues beneath the skin surface. Areas of the mammalian tissue, including human tissue, such as skin surface, associated with jointed regions of the body, such as the joints of the fingers, ankles or knees, can exhibit pronounced movements and changes in their three dimensional contours. Accordingly, in situations where a dressing covers or is in contact with these areas of the body, if the dressing is not able to expand and/or stretch to accommodate changes in body geometry resulting from the movements of the tissues beneath it and/or around it, the likelihood that the dressing would cause discomfort to the wearer or fail by coming off altogether and/or cause trauma to the site of application are all increased, as the dressing counteract the forces resulting from the movements of the tissue surface at or around the site which it covers or is in contact with. Accordingly, in order for a dressing to provide one or more of the aforementioned desired attributes, the dressing may need to not only be able to adhere to the skin surface for a relatively extended amount of time, but also be able to dynamically conform to changing three dimensional contour of the skin surface to which it is applied. Accordingly, in order to provide the dynamic conformability benefit, the dressing of the present invention is designed to be resiliently, freely expandable to a range of three dimensional configurations when one force or a plurality of forces are directed at or applied to the dressing having the pattern of concentric slitted annuli 18.

In any of the above-described embodiments, the dressing 10 is applied to a mammalian tissue or skin so as to, for example, cover or contact a wound, a pressure sore, an ulcer, a wart, a lesion, or a skin surface. In such embodiments, any movement of the skin surface at or around such covered or contacted area can cause and exert a force on the dressing 10 in the thickness direction T thereof. The concentric pattern of annuli 18 is configured such that it is resiliently, freely expandable in the thickness direction T of the dressing 10 (i.e., in the direction of the force) between an initial substantially flat configuration in the LW plane of the dressing 10 and an expanded configuration in the thickness direction T of the dressing 10 (see FIGS. 3A and 3B), the concentric pattern of annuli 18 includes material free regions 16 that are arranged such that, when any movement of the skin surface at or around an area covered or contacted by the dressing 10 causes and exerts a force on the dressing 10, (see FIGS. 3A-3C), the material free regions 16 freely change from their initial closed configuration (or an initial substantially closed configuration), such as in FIG. 3A, to their open configuration (shown as 16' in FIG. 3B), causing expansion of the concentric pattern of annuli 18 in the thickness direction T, from the initial flat configuration in the LW plane to the expanded configuration in the thickness direction T of the dressing 10 (as illustrated in FIG. 3B), wherein once the force is no longer being exerted on the dressing 10 in the thickness direction T the material free regions 16 freely return to their initial closed (or substantially closed) configuration (see FIGS. 3A and 3C), causing the pattern of concentric 18 to freely return to its initial substantially flat configuration in the LW plane (as shown in FIG. 3C). The term "freely" as used herein means that the material used to form the layer of material 12 will not swell so as to restrict or inhibit the opening or closing of the material free regions 16 and/or, once any releasable layer is removed, the layer of material 12 is not attached to any additional layer or substrate so as restrict or inhibit the opening or closing of the material free regions 16. The term "closed", "closed position" or "closed configuration", as used herein with respect to the material free regions 16, means that the material free regions 16 are closed or substantially closed such that there is no, or substantially no, visibility through the material free regions 16 upon visual inspection. The term "open", "open position" or "open configuration", as used herein with respect to the material free regions 16, means that the material free regions 16 are open such that there is visibility through the material free regions 16 upon visual inspection. The term "visibility" as used herein means the ability to see and identify distinct features of animate or inanimate objects.

Figure 3A:
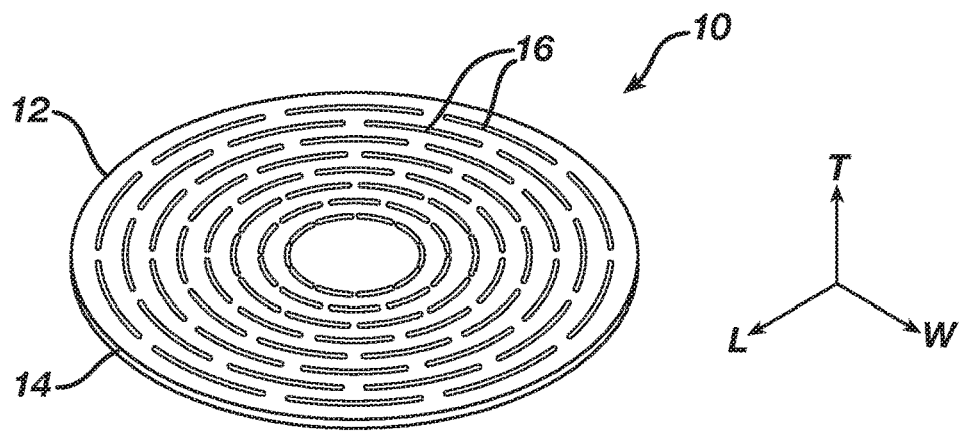
FIG. 3A shows a perspective view of the layer of material of FIG. 1 in a flat configuration in the plane of the layer of material with material free regions of the pattern of concentric slitted annuli of FIG. 2A in a closed position.
Figure 3B:
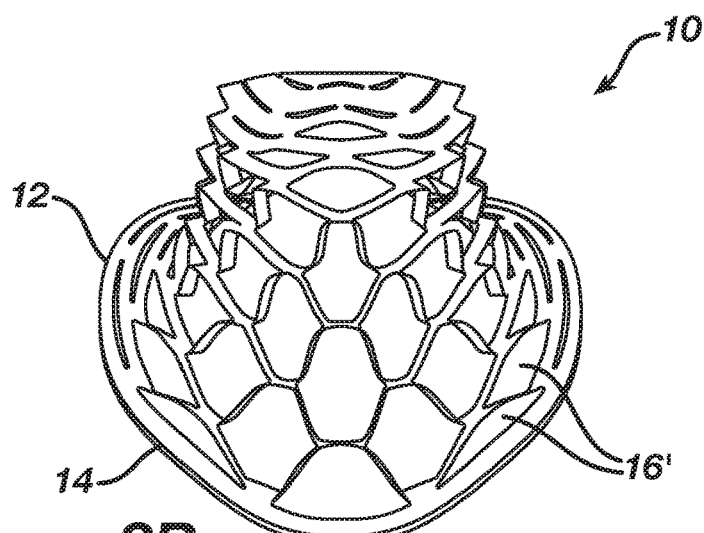
FIG. 3B shows a perspective view of the layer of material of FIG. 1 in an expanded configuration resulting from application of a force in the thickness direction T of the layer of material with the material free regions of the pattern of concentric slitted annuli of FIG. 3A in an open position.
Figure 3C:
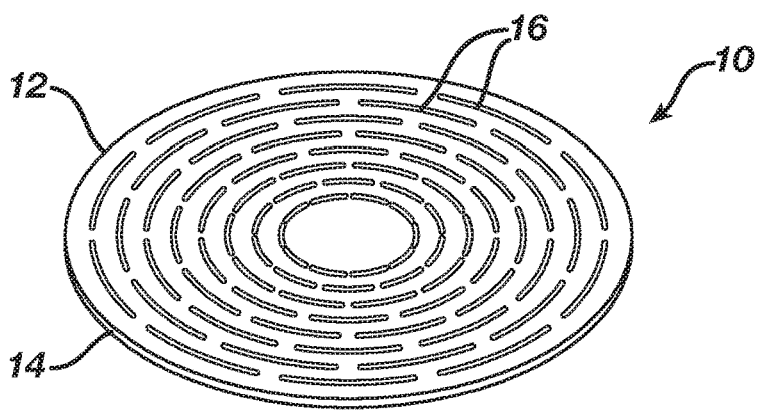
FIG. 3C shows a perspective view of the layer of material of FIG. 3B returned to the flat configuration in the plane of the dressing upon removal of the force in the thickness direction T of the layer of material with material free regions of the pattern of concentric slitted annuli of FIG. 2A returned to the closed position.

In one embodiment, therefore, as shown in FIGS. 3A-3C, the dressing of the present invention mitigates stress and/or strain at the skin surface/dressing interface by dynamically freely expanding at least in its thickness direction to create a three-dimensional shape that is conformable to changing three dimensional contour of the skin surface to which it is applied. In one embodiment, the dressing of the present invention includes a pattern of concentric slitted annuli 18 which forms a three dimensionally expansible portion of the dressing. In one embodiment, the pattern of concentric slitted annuli 18 imparts a three dimensional expansibility to the dressing 10 by having material free regions 16 that are resiliently openable in the thickness direction of the dressing to expand at least a portion of the dressing into a three dimensional configuration that is conformable to a three dimensional contour of the skin surface to which the dressing is applied. In one embodiment, the material free regions 16 of the dressing 10 are resiliently freely openable in the thickness direction T of the dressing in response to an application of a force to the dressing 10, which can happen as a result of a change in the three dimensional contour of the skin surface to which the dressing 10 is applied, to confer a three dimensional configuration to the dressing such that the dressing can conform to a changed three dimensional contour of the skin surface underneath it. In some embodiments, when a force is applied to the pattern of concentric slitted annuli 18 of the dressing 10 one or more of the material free regions 16 of the dressing 10 are resiliently freely opened in the thickness direction T of the dressing 10 to a percentage that is proportionate to the magnitude of the applied force. Thus, when the applied force is lessened or increased the percentage to which the one or more material free regions 16 are opened in the thickness direction T of dressing 10 is respectively decreased or increased.

The extent to which the dressing 10 of the present invention is expansible in its thickness direction T can be modulated by the choice of the materials from which the dressing 10 is made and also by the choice of the number n of the material free regions 16 included in one or more of the concentric annuli of the pattern of concentric slitted annuli 18. In one embodiment, as illustrated in FIG. 2C, the number n of the material free regions 16 is 10 and is the same across all concentric annuli of the pattern of concentric slitted annuli 18. However, other arrangements of the material free regions 16 are also within the purview of the present invention. Contemplated within the purview of the present invention are embodiments in which the number n of the material free regions 16 varies across different concentric annuli of the pattern of concentric slitted annuli 18. Any suitable number of material free regions 16 can be used in the present invention. In some embodiments, the number n of material free regions 16 in any given concentric annulus can range from 2 to 25, optionally from 3 to 25. In some specific embodiments, the number n of material free regions 16 in any given concentric annulus is an integer selected from 2, 3, 4, etc., up to and including 25.

In certain embodiments, the pattern of concentric slitted annuli 18 are formed into the layer of material 12 so as to cover from about 50% to about 100%, optionally at least about 75% to about 100%, optionally from about 90% to about 100%, or optionally 100% (or about 100%), of the surface area of a surface (of both top and bottom planar surfaces) of the layer of material 12. As used herein, "cover 100% of the surface area of a surface of the layer of material" or "100% surface area coverage of the surface of the layer of material" or means that the pattern of concentric slitted annuli cover the entire surface area of the surface of the layer of material and extend to the perimeter edges of the layer of material 12.

The degree of extensibility with which the dressing 10 extends by expansion in its thickness direction T can be measured using an Instru-Met & Instron 1122 & 5543 (Instru-Met Corporation, Union, NJ 07083) with an ASTM D3787 Burst Fixture, including 44.5 mm ID ring clamp and 25.4 mm spherical plunger where the throat of the Burst Fixture is modified by extending it from its original length of 2.5" to a length of 3.75" and where the springs under the screws are removed to ensure clamping forces. The MTS Test Works 4.12 F software application (Instru-Met Corporation, NJ) can also be used to aid in calculations.

Referring to FIG. 2A, in one embodiment, the dressing of the present invention includes spatial intervals 24 between adjacent material free regions 16 within the same concentric annulus of the pattern of concentric slitted annuli 18. In one embodiment, the spatial intervals 24 between material free regions 16 within the same concentric annulus are substantially identical to each other. In some embodiments, the spatial intervals 24 within the same concentric annulus of the pattern of concentric slitted annuli 18 vary in their magnitudes between different pairs of adjacent material free regions 16. In other embodiments, the spatial intervals 24 within the same concentric annulus are substantially identical in their magnitudes but vary in magnitudes between different concentric annuli of the pattern of concentric slitted annuli 18. In some other embodiments, the spatial intervals 24 have magnitudes that do not only differ substantially within any given concentric annulus and between different concentric annuli of the concentric pattern of concentric slitted annuli 18.

In one embodiment, as illustrated in FIG. 2A, the dressing of the present invention includes a plurality of spatial intervals 24 between material free regions 16 within any given concentric annulus wherein each of the spatial intervals 24 has a size that has a minimal value within the innermost concentric annulus and increases in value with each successive radially outer concentric annulus to its maximum value within the outermost concentric annulus of the concentric pattern of annuli 18. In one embodiment, as illustrated in FIG. 4B, each of the spatial intervals 24 within any given concentric annulus subtends an angle θ at the center P, wherein the angle θ has a value that ranges from about 3° to 20°, optionally from about 6° to 20°. In some specific embodiments, the angle θ has a value selected from 3°, 4°, 5°, etc., up to and including 20°.

Referring to FIG. 2B, in one embodiment, the dressing of the present invention includes material free regions 16 each of which has a length 36. As illustrated in FIG. 2B, each of the plurality of the material free regions 16 within any given concentric annulus, has a length 36 that is substantially the same among the plurality of the material free regions 16 within that concentric annulus. In one embodiment, each of the plurality of the material free regions 16 within any given concentric annulus has a length 36 that varies among different concentric annuli but is substantially the same among the plurality of the material free regions 16 within the same concentric annulus. In some embodiments, each of the material free regions 16 has a length 36 that not only varies among the plurality of the material free regions 16 within the same concentric annulus, but also varies between different concentric annuli of the pattern of concentric slitted annuli 18. In one embodiment, as illustrated in FIG. 2B, any of the material free regions 16 of the dressing of the present invention has a length 36 that has a minimal value when the material free region 16 is located within the innermost concentric annulus and increases in value with each successive radially outer concentric annulus to a maximum value when the material free region 16 is located within the outermost concentric annulus.

Figure 5:
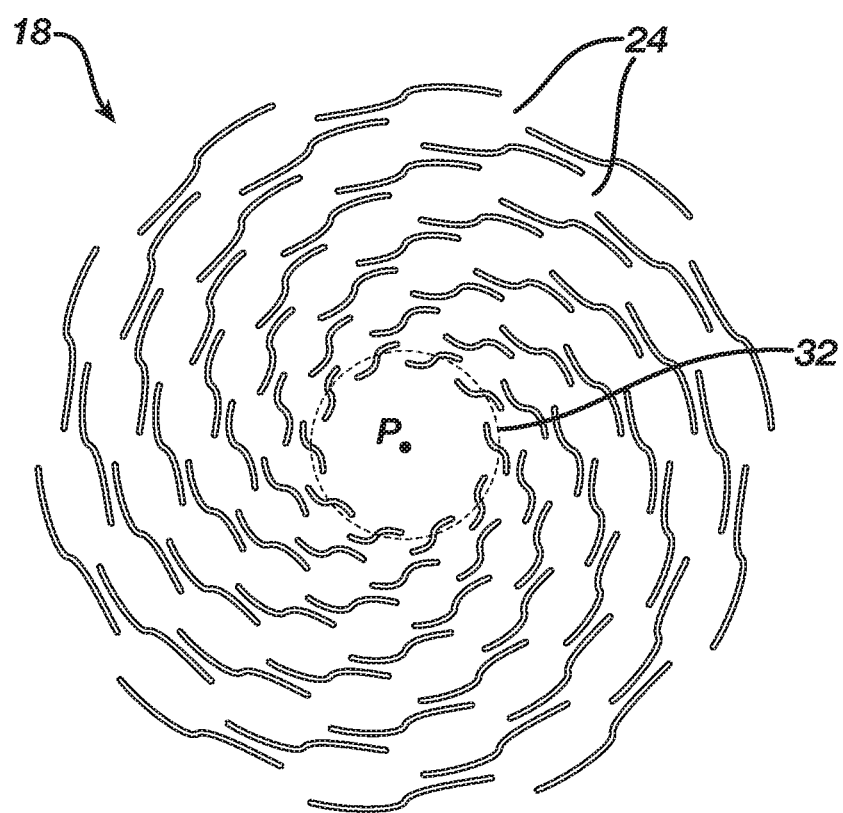
FIG. 5 shows a planar view of a pattern of concentric slitted annuli.

Referring to FIGS. 2A and 5, in one embodiment, the dressing of the present invention includes a plurality of material free regions 16 each of which has a shape which can be any suitable shape so long as the shape would result in a dressing having at least one or more of the properties described elsewhere in the present application. In one embodiment, the dressing of the present invention includes a plurality of material free regions 16 each of which has a curvilinear shape, a sigmoidal shape, a stepped shape, or any combinations thereof Optional Components In some embodiments, the dressing 10 further incorporates on at least one of the top and bottom (or skin facing) surfaces of the layer of material 12, optionally on the bottom (or skin facing) surface, an adhesive to provide adherence of the dressing 10 to a tissue/skin surface. When incorporated onto dressing 10, the adhesive is applied so as not restrict or inhibit the material free regions 16 from being freely movable between their initial closed configuration and open configuration. In general, any of a variety of pressure-sensitive adhesives can be used with the dressing 10. Exemplary pressure-sensitive adhesives, include pressure-sensitive adhesives that are biocompatible with human skin, including water soluble and water insoluble pressure-sensitive adhesives and pressure-sensitive adhesives that are dispersible in an aqueous environment. Examples of commercially available dispersible pressure-sensitive adhesive include: those sold under the trade name of HL-9415-X (available from H.B. Fuller Company). Another suitable adhesive includes about 10-75% by weight of a polyalkyloxazoline polymer, 10-75% by weight of a functional diluent comprising a hydroxy compound or a carboxylic acid compound, and 5-50% by weight of a tackifier. Thus, suitable pressure sensitive adhesive may vary in their compositions. Some may comprise hydrocolloids. The hydrocolloid element used may be any substance that has a good performance in this utilization, as for example, sodium carboxymethylcellulose, pectin, xanthan gum, polysaccharides, sodium or calcium alginates, chitosan, seaweed extract (cageenan), polyaspartic acid, polyglutamic acid, hyaluronic acid or salts and derivatives thereof, among others. Hydrocolloids, such as sodium carboxymethylcellulose and pectin, among others, are agents that form gels as soon as they come into contact with bodily fluids, from wounds, for example. When used in adhesive bandages, these hydrocolloids are combined with elastomers and/or adhesives. Preferably, the adhesive bandage should provide a humid environment but without saturation, cicatrisation, which is a situation suitable for acceleration of the healing.

Other conventional adhesives known for such use in wound dressings may be used with the dressing 10 of the present invention. For example, pressure-sensitive acrylic adhesives, including those containing a resin for increasing adhesion, a cohesion increasing agent, an absorption agent (preferably a polyacrylate superabsorbent, a polyacrylate salt superabsorbent or a mixture thereof), and/or a plasticizer and optionally a pigment.

When applied to the dressing 10 of the present invention, the pressure-sensitive adhesive may be configured in discontinuous patterns, arranged in lines, screen, spray or any other configurations within the purview of a person skilled in the art.

In one embodiment, as illustrated in FIG. 1, the dressing 10 (optionally, including any additional layers 40 [as discussed in more detail below]) further includes a releasable layer 38 in releasable contact with (or releasable attachment to): i) the layer of material 12; or ii) the dressing 10 comprising the layer of material 12. In further embodiments, the releasable layer 38 releasably contacts and covers any adhesive disposed on the layer of material 12. In other embodiments, the releasable layer 38 comprises an adhesive so that the releasable layer 38 adheres to the layer of material 12. In certain embodiments, the releasable layer 38 contacts (or, is releasably attached to) the layer of material 12 or the dressing 10 while the material free regions 16 are in a closed configuration. In some embodiments, the releasable layer 17 contacts (or, is releasably attached to) the layer of material 12 or the dressing 10 such that the material free regions 16 are releasably retained in the closed configuration until such time as the releasable layer 38 is removed from the layer of material 12 or the dressing 10. The releasable layer 38 can be comprised of any suitable material, including, for example, polyethylene, polypropylene, kraft papers, polyester or composites of any of these materials.

Figure 6:
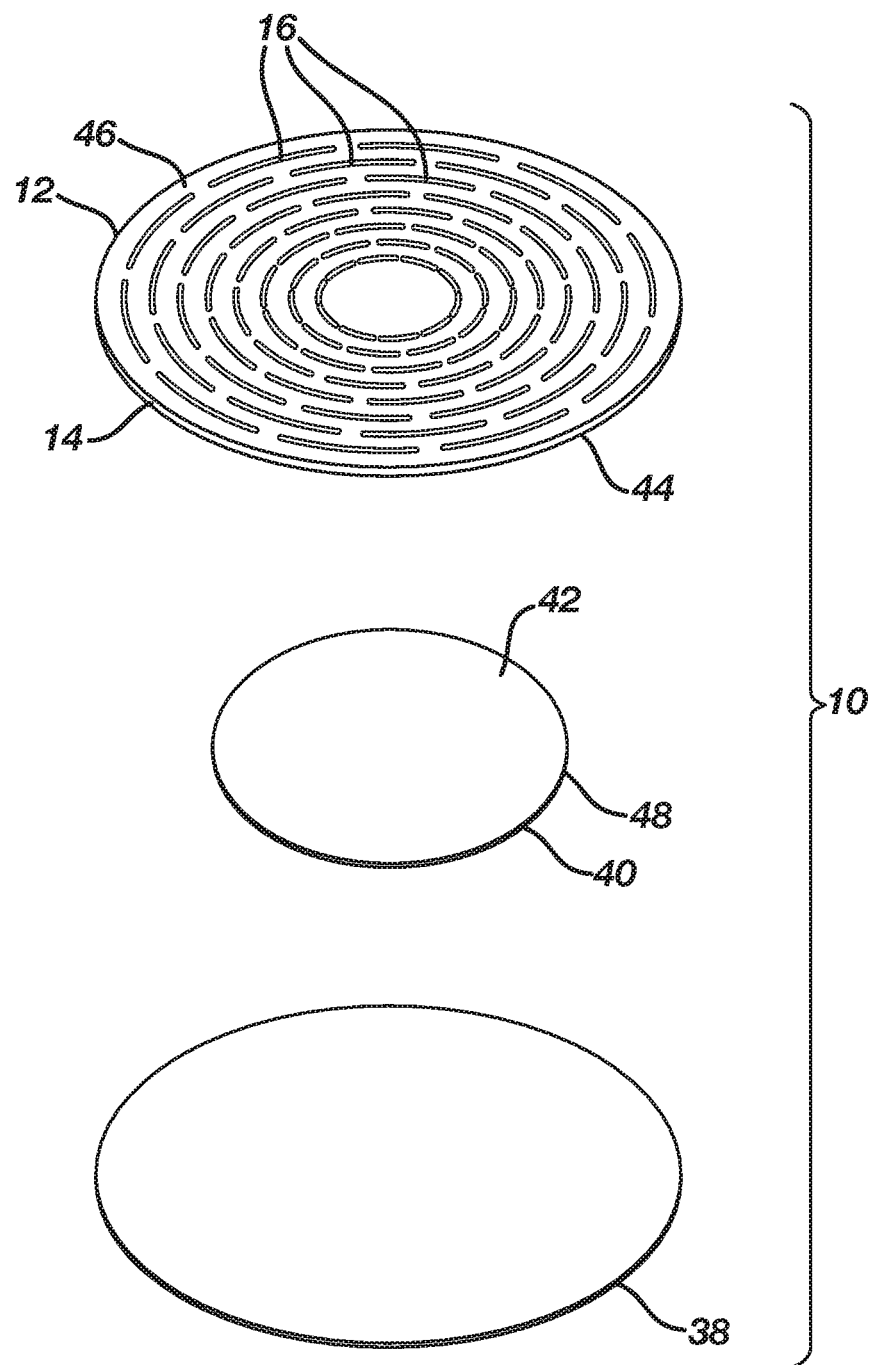
FIG. 6 is an exploded view of a dressing of the present invention showing an additional layer in between the layer of material of the present invention and a releasable layer.
Figure 7:
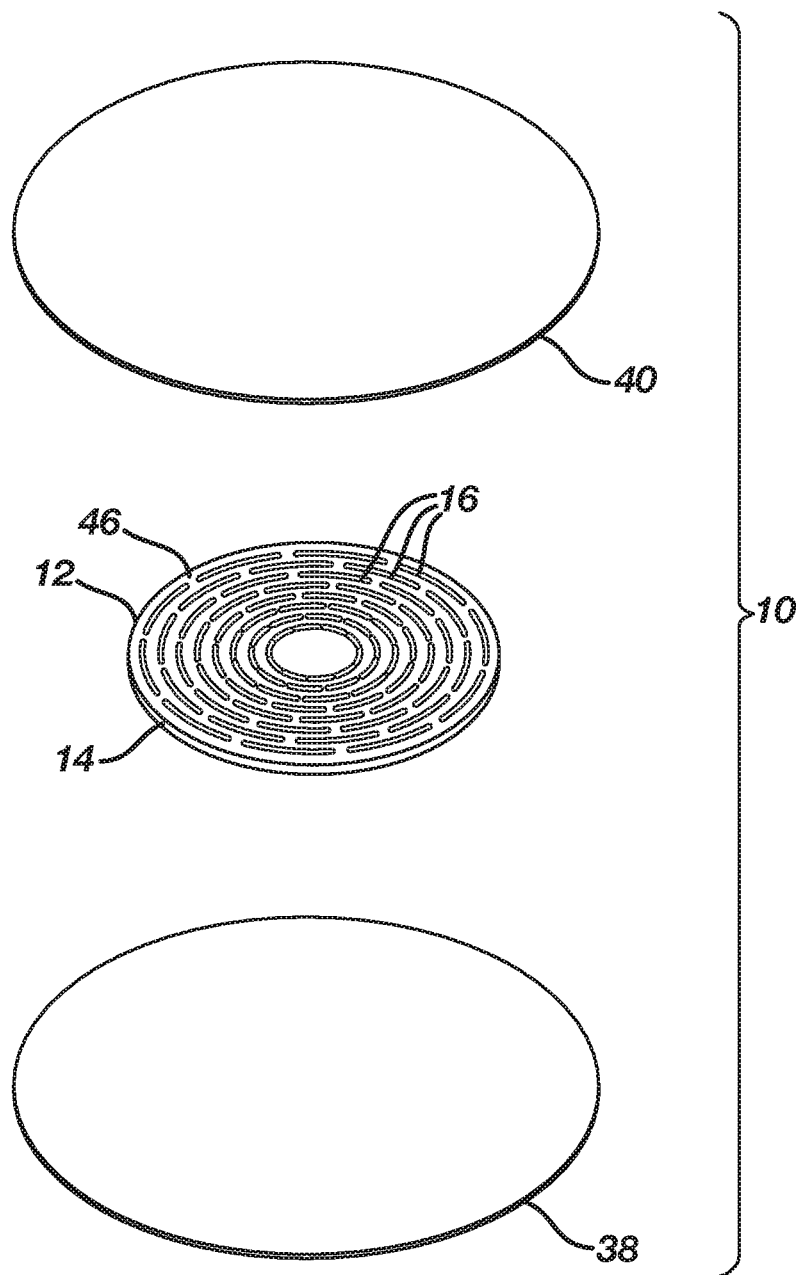
FIG. 7 is an exploded view of a dressing of the present invention showing the layer of material of the present invention in between a backing layer and a releasable layer.
Figure 8:
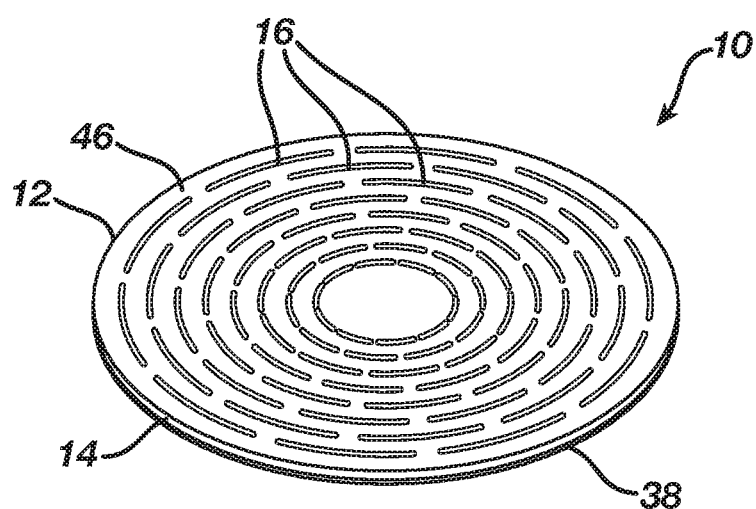
FIG. 8 shows a perspective view of another dressing in accordance with an exemplary embodiment of the present invention.

In one embodiment, as illustrated in FIGS. 6 and 7, the dressing 10 includes one or more layers in addition to the layer of material 12 disposed on the layer of material 12. In one embodiment, the dressing 10 includes additional layer (or substrate layer) 40. In such embodiments, the layer of material 12 is not attached to any additional layer 40 such that additional layer 40 significantly restricts or inhibits the opening or closing of the material free regions 16. In certain embodiments, the additional layer 40 may or may not incorporate the material free regions 16. In embodiments where the additional layer 40 incorporates the material free regions 16, the material free regions 16 in the additional layer 40 form the same or similar pattern units as the concentric annuli pattern units formed by the material free regions 16 in the layer of material 12; in certain of such embodiments, the pattern units of the additional layer 40 are also aligned with the pattern units of the layer of material 12. In another embodiment, the dressing 10 includes one of the one or more additional layers 40 disposed either on the surface side of the layer of material 12 which is opposite the releasable layer 38 or disposed between the layer of material 12 and releasable layer 38. Any one of the one or more additional layers 40 may itself comprise a single or multiple layers. The additional layer 40, in the form of a single or multiple layer, may be incorporated to act as a protective backing layer for layer of material 12 as shown in FIG. 7. Or, such additional layer 40 may act as, or include, a pad layer providing absorbent and/or swelling properties as shown in FIG. 6. In certain embodiments, the additional layer 40 comprises the material free regions 16, and/or the pattern of concentric annuli 18, of the present invention. In certain embodiments, the additional layer 40 is free of or substantially free of the material free regions 16 of the present invention.

In certain embodiments, when additional layer 40 acts as a pad layer, additional layer 40 includes a first surface 42 facing a first side 44 of the layer of material 12, and that has a first surface area 50 and a second surface 48 opposite the first surface 42 and facing the skin, and that has a second surface area 52. Typically, the pad layer can be formed from open work, porous, natural or synthetic fibrous material, such as material used to form gauze. The pad layer typically contacts the skin surface and/or wound to absorb wound exudate or excretions. In certain embodiments, when the additional layer 40 acts as a pad layer, the additional layer 40 can be affixed either directly or indirectly layer of material 12 so that it will not become separated from layer of material 12 during normal use.

When used as a backing layer, additional layer 40 may, in addition to the circular shape illustrated at FIG. 7, have various other shapes, including but not limited to, rectangular, oval, ovoid, or oblong etc. In such an embodiment, the shape of the bandage and tape 10 may be defined by the shape of additional layer 40. In some such embodiments, additional layer 40 may be thin, highly flexible or deformable, water-impervious, and clear or opaque. Generally, in some such embodiments, the thickness of additional layer 40 is between about 0.05 to 0.2 millimeter ("mm") to achieve the forming and flexing characteristics desired.

In certain such embodiments, where additional layer 40 acts as a backing layer, the material used in forming the additional layer 40 should be both conformable to the contours of the body and flexible so as to permit free movement of the body part wearing the product. In certain embodiments, it can be a woven or nonwoven fabric, a film or a foam. Polymeric materials useful in forming backing layers include polyolefin (such as polyethylene), polyurethane, and polyvinylchloride. Other examples of backings include, but are not limited to, nonwoven, woven, or knitted fabrics such as cotton, polyester, polyurethane, rayon and the like.

Polyethylene film may be optional used to form additional layer 40 where additional layer 40 acts as a backing layer 40, and, in such instances, particularly effective results can be achieved with stretchable, elastomeric films formed of polyurethane, which has the further advantage of gas (including water vapor) transmissibility. It is to be understood, however, that, in such instances, other flexible, water insoluble polymeric films known in the art may be used. Furthermore, where additional layer 40 is used as a backing layer, additional layer 40 may be formed from closed-cell polymeric foam, particularly one with an integral skin covering the side of the closed-cell polymeric foam facing away from the skin of the user. In certain such embodiments, foam layers formed of polyurethane or polyethylenes are suitable, while other polymeric foams having similar properties may be used. In other embodiments, where additional layer 40 is used as a backing layer, additional layer 40 may be made from other polyolefins, vinyl polyethylene acetate, textile non-woven fabrics, rubber, or other materials known in the adhesive article art. In certain embodiments, polymers used to form additional layer 40 where additional layer 20 acts as a backing layer generally have viscosity of from about 500 to 500,000 centipoises at temperatures of about 190° C., or from about 1,000 to 30,000 centipoises at temperatures of about 190° C., or from about 3,000 to 15,000 centipoises at temperatures of about 190° C.

In certain embodiments, where additional layer 40 acts as a backing layer, additional layer 40 may be impermeable to liquid, but permeable to gas, which allows the wound and the skin to which the bandage and tape 10 of the present invention is adhered to breathe. In one embodiment, where additional layer 40 acts as a backing layer, additional layer 40 may have pores of such a size that will allow only the passage of gases, which have molecules of extremely small size.

Finally, where additional layer 40 acts as a backing layer, additional layer 40 may be perforated for still further ventilation of the skin. In certain such embodiments, perforations may be circular in area and have a range of diameters, such as from about 0.1 to about 0.8 millimeters. In certain other embodiments, however, where additional layer 40 acts as a backing layer, additional layer 40 may, when necessary, be totally impermeable to gases.

The present invention is further described by the following examples which are presented for purposes of illustration and comparison.

It is to be understood that at least some of the figures and descriptions of the invention have been simplified to focus on elements that are relevant for a clear understanding of the invention.

Further, to the extent that any method does not rely on the particular order of steps set forth herein, the particular order of the steps should not be construed as limitation on the claims. The claims directed to any such method of the present invention should not be limited to the performance of their steps in the order written, and one skilled in the art can readily appreciate that the steps may be varied and still remain within the spirit and scope of the present invention.

Embodiments of the Present Invention

1. A dressing comprising:
a layer of non-cellulosic material having:
(i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
(ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters,
wherein the plurality of the material free regions is arranged end to end, separated by a plurality of spatial intervals, such that any material free region In located in any concentric annulus I subtends a non-zero valued angle, con, at the center point P, where n represents the number identifying a material free region in an annulus having material free regions arranged numerically consecutively in such annulus,
wherein the sum of the non-zero valued angles subtended by the plurality of the material free regions at the center point P, within any one of the concentric annuli, is less than 360 degrees, and
wherein the material free regions of any one of the concentric annuli are in a radially staggered relation with respect to the material free regions in any adjacent inner and/or adjacent outer concentric annulus.

2. The dressing of embodiment 1 further including one or more intervening concentric annuli disposed between the innermost and outermost concentric annuli.

3. The dressing of embodiments 1 and/or 2, wherein any of the one or more intervening concentric annuli has a larger diameter than the diameter of any adjacent inner concentric annulus with respect to the intervening concentric annulus.

4. The dressing of any one or combination of the preceding embodiments, wherein any material free region of any radially concentric annulus has an axis of symmetry bisecting the angle subtended by the material free region at the center point P.

5. The dressing of any one or combination of the preceding embodiments, wherein any material free region of the radially outermost and/or innermost concentric annulus has an axis of symmetry bisecting the angle subtended by the material free region at the center point P.

6. The dressing of any one or combination of the preceding embodiments, wherein:
(a) any material free region In further has an axis of symmetry that bisects the non-zero valued angle $\alpha_{In}$;
(b) any material free region Kn located in any concentric annulus K that is adjacent to concentric annulus I and proximate to material free region In, subtends a non-zero valued angle $\alpha_{Kn}$ at the center point P and has an axis of symmetry that bisects the non-zero valued angle $\alpha_{Kn}$;
(c) the axis of symmetry of the material free region In is staggered by an angle φ from the axis of symmetry of the material free region Kn; and
(d) the angle φ has a value that falls within a range specified by the equation: $0° < \varphi < (\alpha_{In} + \alpha_{Kn})$.

7. The dressing of any one or combination of the preceding embodiments, wherein the axis of symmetry of any material free region of the radially innermost concentric annulus is radially staggered from the axis of symmetry of any proximate material free regions located in the radially outermost concentric annulus, by an angle φ that has a value ranging from about 5° to about 40°.
8. The dressing of any one or combination of the preceding embodiments, wherein the axis of symmetry of any material free region in any one of the concentric annuli is radially staggered from the axis of symmetry of any proximate material free regions located in any adjacent radially inner or outer concentric annulus with respect to the concentric annulus by an angle φ that has a value ranging from about 5° to about 30°.
9. The dressing of any one or combination of the preceding embodiments, wherein the innermost concentric annulus has a diameter ranging from about 0.125" to about 3.5".
10. The dressing of any one or combination of the preceding embodiments, wherein the outermost concentric annulus has a diameter ranging from about 0.125" to about 0.25".
11. The dressing of any one or combination of the preceding embodiments, wherein the innermost concentric annulus has a diameter ranging from about 0.125 to about 0.5" and the outermost concentric annulus has a diameter ranging from about 0.5" to about 1".
12. The dressing of any one or combination of the preceding embodiments, wherein the innermost concentric annulus has a diameter of about 0.125".
13. The dressing of any one or combination of the preceding embodiments, wherein the outermost concentric annulus has a diameter of about 0.5".
14. The dressing of any one or combination of the preceding embodiments, wherein the innermost concentric annulus has a diameter of about 0.125" and the outermost concentric annulus has a diameter of about 0.5".
15. The dressing of any one or combination of the preceding embodiments, wherein each concentric annulus has a concentric centerline.
16. The dressing of any one or combination of the preceding embodiments, wherein the pattern of concentric slitted annuli has equal radial spacing between neighboring concentric centerlines of successive pairs of neighboring concentric annuli.
17. The dressing of any one or combination of the preceding embodiments, wherein any pair of neighboring concentric centerlines of a pair of neighboring concentric annuli is separated by a radial spacing that varies among different pairs of neighboring concentric centerlines of successive pairs of neighboring concentric annuli of the pattern of concentric slitted annuli.
18. The dressing of any one or combination of embodiments 1-15, wherein the pattern of concentric slitted annuli has a radial spacing between pairs of neighboring concentric centerlines of neighboring concentric annuli that increases radially outwardly from the center point P.
19. The dressing of any one or combination of embodiments 1-15, wherein the pattern of concentric slitted annuli has a radial spacing between pairs of neighboring concentric centerlines of neighboring concentric annuli that decreases radially outwardly from the center point P.
20. The dressing of any one or combination of embodiments 1-15, wherein the pattern of concentric slitted annuli has a radial spacing between each pair of neighboring concentric centerlines of successive pairs of neighboring concentric annuli that varies among different pairs of neighboring concentric annuli.
1 21. The dressing of any one or combination of embodiments 1-15, wherein any pair of adjacent concentric annuli is spaced apart radially by a distance that is the difference between the respective radial distances of the adjacent concentric annuli from the center point P.
22. The dressing of any one or combination of the preceding embodiments, wherein the layer of material is expansible in the thickness direction thereof
23. The dressing of any one or combination of embodiments 1-21, wherein the layer of material is resiliently expansible in the thickness direction in response to any force that is applied to the portion of the dressing having the pattern of concentric slitted annuli, whereby the resilient expansion of the layer of material is a percentage that is proportional to the magnitude of the force being applied thereto.
24. The dressing of any one or combination of the preceding embodiments, wherein each of the plurality of spatial intervals separating the plurality of material free regions within any given concentric annulus has a size that has a minimal value within the innermost concentric annulus and increases in value with each successive radially outer concentric annulus to its maximum value within the outermost concentric annulus of the pattern of concentric slitted annuli.
25. The dressing of any one or combination of the preceding embodiments, wherein any spatial interval within any given concentric annulus subtends an angle θ at the center P.
26. The dressing of embodiment 25, wherein the angle θ has a value that ranges from about 3° to 20°.
27. The dressing of any one of or combination of embodiments 25 and/or 26, wherein the angle θ has from about 6° to 20°.
26. A dressing comprising:
a. a layer of material having:
   (i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
   (ii) a plurality of material free regions, each of the material free regions extends through the thickness of the layer of material and the plurality of the material free regions is arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters; and
b. a releasable liner releasably contacting the layer of material;
wherein the material free regions are arranged end to end, separated by spatial intervals, such that any material free region In located in any concentric annulus I subtends a non-zero valued angle $\alpha_{I_n}$ at the center point P where n represents the number identifying a material free region in an annuli having material free regions arranged numerically consecutively in such annuli, wherein the sum of the non-zero valued angles subtended by the plurality of the material free regions at the center point P, in any one of the concentric annuli, is less than 360 degrees, and wherein the material free regions of any one of the concentric annuli are in a radially staggered relation with the material free regions in any adjacent inner and/or adjacent outer concentric annulus.

27. The dressing of embodiment 26, wherein any material free region In further has an axis of symmetry that bisects the non-zero valued angle $\alpha_{In}$.

28. The dressing of any one or combination of embodiments 26 and/or 27, wherein any material free region Kn located in any concentric annulus K that is adjacent to concentric annulus I and proximate to material free region In subtends a non-zero valued angle $\alpha_{Kn}$ at the center point P and has an axis of symmetry that bisects the non-zero valued angle $\alpha_{Kn}$, wherein the axis of symmetry of the material free region In and the axis of symmetry of the material free region Kn are staggered relative to one another by an angle $\varphi$ that has a value falling within a range specified by the equation: $0° < \varphi < (\alpha_{In} + \alpha_{Kn})$.

29. The dressing of embodiment 26, wherein the angle $\varphi$ has a value ranging from about 5° to about 40°.

30. The dressing of embodiment 26, wherein the angle $\varphi$ has a value ranging from about 5° to about 30°.

31. The dressing of any one or combination of embodiments 26-30, wherein each of the angles $\alpha_{In}$ and $\alpha_{Kn}$ has a value ranging from about 20° to about 177°.

32. The dressing of any one or combination of embodiments 26-31, wherein each of the angles $\alpha_{In}$ and $\alpha_{Kn}$ has a value ranging from about 20° to about 90°.

33. The dressing of any one or combination of embodiments 26-32, wherein each of the angles $\alpha_{In}$ and $\alpha_{Kn}$ has a value ranging from about 20° to about 60°.

34. The dressing of any one or combination of embodiments 26-33, wherein each of the angles $\alpha_{In}$ and $\alpha_{Kn}$ has a value ranging from about 30° to about 60°.

35. A dressing comprising:
   a.) a layer of material having top and bottom surfaces, the layer of material having a thickness direction (T) and configured to be resiliently freely expandable in the thickness direction T by any force applied in the thickness direction T from a skin surface at or around an area covered or contacted by the dressing, the layer of material having mutually orthogonal length (L) and width (W) directions jointly defining a horizontal plane ("the LW plane") of the layer of material, the LW plane being orthogonal to the thickness direction T and the layer of material having a thickness taken in the thickness direction T;
   the layer of material includes a concentric pattern of annuli having a center point P and configured such that it is resiliently freely expandable in the thickness direction T of the layer of material between an initial substantially flat configuration in the LW plane of the layer of material and an expanded configuration in the thickness direction T of the layer of material,
   the concentric pattern of annuli includes a plurality of material free regions that are freely changeable between an initial closed configuration and an open configuration, and the material free regions being arranged such that when a force is applied in the thickness direction T, from a skin surface at or around an area covered or contacted by the dressing, one or more of the material free regions freely change from the initially closed configuration to the open configuration;
   b.) an adhesive on at least one of the surfaces of the layer of material;
   wherein the concentric pattern of annuli and the layer of material expand in the thickness direction T to an expanded configuration,
   wherein once the force is no longer being applied on the layer of material, the one or more material free regions freely return to their initially closed configuration,
   causing the pattern of concentric slitted annuli to freely return to its initial substantially flat configuration in the LW plane of the material layer.

36. The dressing of embodiment 35, wherein the plurality of the material free regions is arranged end to end, separated by spatial intervals, such any material free region In located in any concentric annulus I subtends a non-zero valued angle $\alpha_{In}$ at the center point P, where n represents the number identifying a material free region in an annuli having material free regions arranged numerically consecutively in such annuli.

37. The dressing of any one or combination of embodiments 35 and 36, wherein the sum of the non-zero valued angles subtended by the plurality of the material free regions at the center point P, within any one of the concentric annuli, is less than 360 degrees.

38. The dressing of any one or combination of embodiments 35-37, wherein the material free regions of any one of the concentric annuli are in a radially staggered relation with respect to the material free regions in any adjacent inner and/or adjacent outer concentric annulus.

39. The dressing of any one or combination of embodiments 36-38, wherein material free region In has an axis of symmetry that bisects the non-zero valued angle $\alpha_{In}$.

40. The dressing of embodiment 39, wherein any material free region Kn located in any concentric annulus K that is adjacent to concentric annulus I and proximate to material free region In, not only subtends a non-zero valued angle $\alpha_{kl}$ at the center point P, but also has an axis of symmetry that bisects the non-zero valued angle $\alpha_{Kn}$, wherein the axis of symmetry of the material free region In and the axis of symmetry of the material free region Kn are staggered relative to one another by an angle $\varphi$ that has a value falling within a range specified by the equation: $0° < \varphi < (\alpha_{In} + \alpha_{Kn})$.

41. The dressing of embodiment 40, wherein the angle $\varphi$ has a value ranging from about 5° to about 40°.

42. The dressing of any one or combination of embodiments 40 and/or 41, wherein the angle $\varphi$ has a value ranging from about 5° to about 30°.

43. The dressing of embodiment 40, wherein each of angles $\alpha_{In}$ and $\alpha_{Kn}$ has a value ranging from about 20° to about 177°.

44. The dressing of any one or combination of the preceding embodiments, wherein each of angles $\alpha_{In}$ and $\alpha_{Kn}$ has a value ranging from about 20° to about 90°.

45. The dressing of any one or combination of the preceding embodiments, wherein each of angles $\alpha_{In}$ and $\alpha_{Kn}$ has a value ranging from about 20° to about 60°.

46. The dressing of any one or combination of the preceding embodiments, wherein each of angles $\alpha_{In}$ and $\alpha_{Kn}$ has a value ranging from about 30° to about 60°.

47. A dressing comprising:
a. one or more layers comprising a layer of material having:
   (i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
   (ii) a plurality of material free regions, each of the material free regions extends through the thickness of the layer of material and the plurality of the material free regions is arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters; and
b. a releasable liner releasably contacting the one or more layers,
wherein the material free regions are arranged end to end, separated by spatial intervals, such that any material free region In located in any concentric annulus I subtends a non-zero valued angle $\alpha_{In}$ at the center point P where n represents the number identifying a material free region in an annuli having material free regions arranged numerically consecutively in such annuli.

What is claimed is:
1. A dressing comprising:
a layer of non-cellulosic material having:
   (i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
   (ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters,
wherein the plurality of the material free regions is arranged end to end, separated by a plurality of spatial intervals, such that any material free region In located in any concentric annulus I subtends a non-zero valued angle, $\alpha_{In}$, at the center point P, where n represents the number identifying a material free region in an annuli having material free regions arranged numerically consecutively in such annulus,
wherein the sum of the non-zero valued angles subtended by the plurality of the material free regions at the center point P, within any one of the concentric annuli, is less than 360 degrees, and
wherein the material free regions of any one of the concentric annuli are in a radially staggered relation with respect to the material free regions in any adjacent inner and/or adjacent outer concentric annulus,
wherein material free regions that are resiliently openable in the thickness direction T of the dressing to expand at least a portion of the dressing into a three dimensional configuration that is conformable to a three dimensional contour of a skin surface to which the dressing may be applied.

2. The dressing of claim 1 further including one or more intervening concentric annuli disposed between the innermost and outermost concentric annuli.

3. The dressing of claim 2, wherein any of the one or more intervening concentric annuli has a larger diameter than the diameter of any adjacent inner concentric annulus with respect to the intervening concentric annulus.

4. The dressing of claim 1, wherein the innermost concentric annulus has a diameter ranging from about 0.125" to about 3.5".

5. The dressing of claim 1, wherein the outermost concentric annulus has a diameter ranging from about 0.125" to about 0.25".

6. The dressing of claim 1, wherein the innermost concentric annulus has a diameter ranging from about 0.125 to about 0.5" and the outermost concentric annulus has a diameter ranging from about 0.5" to about 1".

7. The dressing of claim 1, wherein any pair of adjacent concentric annuli is spaced apart radially by a distance that is the difference between the respective radial distances of the adjacent concentric annuli from the center point P.

8. The dressing of claim 1, wherein each of the plurality of spatial intervals separating the plurality of material free regions within any given concentric annulus has a size that has a minimal value within the innermost concentric annulus and increases in value with each successive radially outer concentric annulus to its maximum value within the outermost concentric annulus of the pattern of concentric slitted annuli.

9. The dressing of claim 1, wherein any spatial interval within any given concentric annulus subtends an angle θ at the center P and further wherein the angle θ has a value that ranges from about 3° to 20°.

10. A dressing comprising:
a layer of non-cellulosic material having:
   (i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and
   (ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters, wherein the plurality of the material free regions is arranged end to end, separated by a plurality of spatial intervals, such that any material free region In located in any concentric annulus I subtends a non-zero valued angle, $\alpha_{In}$, at the center point P, where n represents the number identifying a material free region in an annulus having material free regions arranged numerically consecutively in such annulus, wherein the sum of the non-zero valued angles subtended by the plurality of the material free regions at the center point P, within any one of the concentric annuli, is less than 360 degrees, and wherein the material free regions of any one of the concentric annuli are in a radially staggered relation with respect to the material free regions in any adjacent inner and/or adjacent outer concentric annulus, wherein material free regions are resiliently openable in the thickness direction T of the dressing to expand at least a portion of the dressing into a three dimensional configuration that is conformable to a three dimensional contour of a skin surface to which the dressing may be applied, and wherein any material free region of any radially concentric annulus has an axis of symmetry bisecting the angle subtended by the material free region at the center point P.

11. The dressing of claim 10, wherein the axis of symmetry of any material free region of the radially innermost concentric annulus is radially staggered from the axis of symmetry of any proximate material free regions located in the radially outermost concentric annulus, by an angle φ that has a value ranging from about 5° to about 40°.

12. The dressing of claim 10, wherein the axis of symmetry of any material free region in any one of the concentric annuli is radially staggered from the axis of symmetry of any proximate material free regions located in any adjacent radially inner or outer concentric annulus with respect to the concentric annulus by an angle φ that has a value ranging from about 5° to about 30°.

13. A dressing comprising:

a layer of non-cellulosic material having:

(i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and (ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters, wherein the plurality of the material free regions is arranged end to end, separated by a plurality of spatial intervals, such that any material free region In located in any concentric annulus I subtends a non-zero valued angle, $\alpha_{In}$, at the center point P, where n represents the number identifying a material free region in an annulus having material free regions arranged numerically consecutively in such annulus, wherein the sum of the non-zero valued angles subtended by the plurality of the material free regions at the center point P, within any one of the concentric annuli, is less than 360 degrees, and wherein the material free regions of any one of the concentric annuli are in a radially staggered relation with respect to the material free regions in any adjacent inner and/or adjacent outer concentric annulus, wherein material free regions are resiliently openable in the thickness direction T of the dressing to expand at least a portion of the dressing into a three dimensional configuration that is conformable to a three dimensional contour of a skin surface to which the dressing may be applied, and wherein:

(a) any material free region In further has an axis of symmetry that bisects the non-zero valued angle $\alpha_{In}$;

(b) any material free region Kn located in any concentric annulus K that is adjacent to concentric annulus I and proximate to material free region In, subtends a non-zero valued angle $\alpha_{Kn}$ at the center point P and has an axis of symmetry that bisects the non-zero valued angle $\alpha_{Kn}$;

(c) the axis of symmetry of the material free region In is staggered by an angle φ from the axis of symmetry of the material free region Kn; and (d) the angle φ has a value that falls within a range specified by the equation: $0° < \varphi < (\alpha_{In} + \alpha_{Kn})$.

14. A dressing comprising:

a layer of non-cellulosic material having:

(i) a length direction (L), a width direction (W), and a thickness direction (T) respectively defining axes in three mutually orthogonal directions, the length direction (L) and the width direction W defining a horizontal plane ("the LW plane"), and the thickness direction (T) defining an up-down direction or a vertical direction relative to the LW plane, the layer of material having a thickness taken in the thickness direction; and (ii) a plurality of material free regions, each of the material free regions extending through the thickness of at least a portion of the layer of material and the plurality of the material free regions being arranged in the form of a pattern of concentric slitted annuli having a center point (P) in the LW plane, the pattern of concentric slitted annuli having, relative to center point P, a radially innermost concentric annulus and a radially outermost concentric annulus, the innermost and the outermost concentric annuli respectively having the shortest and the longest diameters, wherein the plurality of the material free regions is arranged end to end, separated by a plurality of spatial intervals, such that any material free region In located in any concentric annulus I subtends a non-zero valued angle, $\alpha_{In}$, at the center point P, where n represents the number identifying a material free region in an annulus having material free regions arranged numerically consecutively in such annulus, wherein the sum of the non-zero valued angles subtended by the plurality of the material free regions at the center point P, within any one of the concentric annuli, is less than 360 degrees, and wherein the material free regions of any one of the concentric annuli are in a radially staggered relation with respect to the material free regions in any adjacent inner and/or adjacent outer concentric annulus, wherein material free regions are resiliently openable in the thickness direction T of the dressing to expand at least a portion of the dressing into a three dimensional configuration that is conformable to a three dimensional contour of a skin surface to which the dressing may be applied, and wherein each concentric annulus has a concentric centerline.

15. The dressing of claim 14, wherein the pattern of concentric slitted annuli has equal radial spacing between neighboring concentric centerlines of successive pairs of neighboring concentric annuli.

16. The dressing of claim 14, wherein any pair of neighboring concentric centerlines of a pair of neighboring concentric annuli is separated by a radial spacing that varies among different pairs of neighboring concentric centerlines of successive pairs of neighboring concentric annuli of the pattern of concentric slitted annuli.

17. The dressing of claim 16, wherein the pattern of concentric slitted annuli has a radial spacing between pairs of neighboring concentric centerlines of neighboring concentric annuli that increases radially outwardly from the center point P.

18. The dressing of claim 16, wherein the pattern of concentric slitted annuli has a radial spacing between pairs of neighboring concentric centerlines of neighboring concentric annuli that decreases radially outwardly from the center point P.

19. The dressing of claim 14, wherein the pattern of concentric slitted annuli has a radial spacing between each pair of neighboring concentric centerlines of successive pairs of neighboring concentric annuli that varies among different pairs of neighboring concentric annuli.

* * * * *